United States Patent
Crutchley et al.

(10) Patent No.: US 9,549,896 B2
(45) Date of Patent: Jan. 24, 2017

(54) BIOERODIBLE PATCH COMPRISING A POLYAPHRON DISPERSION

(75) Inventors: Nigel Crutchley, Leatherhead (GB); Steen Sindet-Pedersen, Leatherhead (GB); Stephen Lenon, Leatherhead (GB)

(73) Assignee: DRUG DELIVERY SOLUTIONS LIMITED, Leatherhead, Surry (GB)

( * ) Notice: Subject to any disclaimer, the term of this patent is extended or adjusted under 35 U.S.C. 154(b) by 0 days.

(21) Appl. No.: 12/666,491

(22) PCT Filed: Jun. 26, 2008

(86) PCT No.: PCT/GB2008/002197
§ 371 (c)(1),
(2), (4) Date: Apr. 13, 2010

(87) PCT Pub. No.: WO2009/001092
PCT Pub. Date: Dec. 31, 2008

(65) Prior Publication Data
US 2010/0189770 A1 Jul. 29, 2010

Related U.S. Application Data

(60) Provisional application No. 60/929,394, filed on Jun. 26, 2007.

(30) Foreign Application Priority Data

Jun. 26, 2007 (EP) ..................................... 07252591

(51) Int. Cl.
| | |
|---|---|
| A61K 9/10 | (2006.01) |
| A61K 9/70 | (2006.01) |
| A61K 38/28 | (2006.01) |
| A61K 31/465 | (2006.01) |
| A61K 9/00 | (2006.01) |
| A61K 9/107 | (2006.01) |
| A61K 9/12 | (2006.01) |

(52) U.S. Cl.
CPC ............. *A61K 9/006* (2013.01); *A61K 31/465* (2013.01); *A61K 38/28* (2013.01); *A61K 9/107* (2013.01); *A61K 9/1075* (2013.01); *A61K 9/122* (2013.01)

(58) Field of Classification Search
None
See application file for complete search history.

(56) References Cited

U.S. PATENT DOCUMENTS

| | | | |
|---|---|---|---|
| 4,486,333 A | 12/1984 | Sebba | |
| 4,533,546 A | 8/1985 | Kishi et al. | |
| 4,871,723 A | 10/1989 | Makino et al. | |
| 4,900,552 A * | 2/1990 | Sanvordeker et al. | 424/422 |
| 4,936,933 A | 6/1990 | Yabsley et al. | |
| 4,944,938 A | 7/1990 | Potini | |
| 4,999,198 A | 3/1991 | Barnett et al. | |
| 5,346,701 A * | 9/1994 | Heiber et al. | 424/435 |
| 5,474,979 A | 12/1995 | Ding et al. | |
| 5,573,757 A | 11/1996 | Riess et al. | |
| 5,645,856 A | 7/1997 | Lacy et al. | |
| 5,660,858 A | 8/1997 | Parikh et al. | |
| 5,763,426 A | 6/1998 | Hansen et al. | |
| 5,840,881 A | 11/1998 | Uda et al. | |
| 5,952,383 A | 9/1999 | Metziger et al. | |
| 5,955,097 A | 9/1999 | Tapolsky et al. | |
| 5,990,100 A | 11/1999 | Rosenberg et al. | |
| 6,096,338 A | 8/2000 | Lacy et al. | |
| 6,165,479 A | 12/2000 | Wheeler | |
| 6,200,581 B1 | 3/2001 | Lin et al. | |
| 6,238,678 B1 | 5/2001 | Oblong et al. | |
| 6,538,039 B2 | 3/2003 | Laurent | |
| 6,562,370 B2 | 5/2003 | Luo et al. | |
| 6,585,997 B2 | 7/2003 | Moro et al. | |
| 6,599,527 B1 | 7/2003 | Leigh et al. | |
| 6,753,013 B1 | 6/2004 | Didriksen et al. | |
| 6,787,529 B2 | 9/2004 | Hoy et al. | |
| 7,001,607 B1 | 2/2006 | Menz et al. | |
| RE39,706 E | 6/2007 | Hansen et al. | |
| 8,263,580 B2 | 9/2012 | Buchta et al. | |
| 8,298,515 B2 | 10/2012 | Buchta et al. | |
| 8,629,128 B2 | 1/2014 | Buchta et al. | |
| 8,633,162 B2 | 1/2014 | Acheampong et al. | |
| 8,642,556 B2 | 2/2014 | Acheampong et al. | |
| 8,648,008 B2 | 2/2014 | Misra et al. | |
| 8,669,111 B2 | 3/2014 | Rehder et al. | |
| 2005/0001643 A1 | 1/2005 | Yoshida et al. | |
| 2005/0002546 A1 | 1/2005 | Florent et al. | |

(Continued)

FOREIGN PATENT DOCUMENTS

| | | |
|---|---|---|
| CN | 1351499 A | 5/2002 |
| CN | 1832731 A | 9/2006 |

(Continued)

OTHER PUBLICATIONS

Montalto, S. J. Master's Thesis (1984); University of Rhode Island; pp. 1-84.*
U.S. Office Action cited in U.S. Appl. No. 14/003,871 mailed Jun. 24, 2015.
U.S. Office Action cited in U.S. Appl. No. 12/450,183 mailed Aug. 26, 2015.
Adams, "Vitamin D myths, facts and statistics," Natural News, 2005, Abstract.
Ashcroft et al., "Systematic Review . . . Plaque Psoriasis" British Medical Journal, 320:963-967 (2000).
Charakida et al., "Calcipotriol/betamethasone dipropionate for the treatment of psoriasis," Expert Opin. Pharmacother, 7(5):597-606 (2006).
Office Action for Chinese Patent Application No. 200880008496.X (with English translation) (11 pages).

(Continued)

*Primary Examiner* — Kevin S Orwig
(74) *Attorney, Agent, or Firm* — Merchant & Gould P.C.

(57) ABSTRACT

A bioerodible patch comprising at least one bioadhesive layer and at least one non-bioadhesive layer, wherein the bioadhesive layer comprises at least one polyaphron dispersion and at least one bioadhesive polymer, and wherein the polyaphron dispersion comprises at least one pharmaceutically active agent.

26 Claims, No Drawings

(56) References Cited

U.S. PATENT DOCUMENTS

| | | |
|---|---|---|
| 2005/0020546 A1 | 1/2005 | Laidlaw et al. |
| 2005/0026877 A1 | 2/2005 | Chen et al. |
| 2005/0082515 A1 | 4/2005 | Masuichi et al. |
| 2005/0147658 A1* | 7/2005 | Tapolsky et al. ............ 424/448 |
| 2005/0238676 A1 | 10/2005 | Gladman et al. |
| 2005/0281749 A1 | 12/2005 | Willcox et al. |
| 2005/0281750 A1 | 12/2005 | Willcox et al. |
| 2005/0281754 A1 | 12/2005 | Willcox et al. |
| 2005/0281755 A1 | 12/2005 | Zarif et al. |
| 2005/0281848 A1 | 12/2005 | Zanutto et al. |
| 2005/0281850 A1 | 12/2005 | Zanutto et al. |
| 2005/0282788 A1 | 12/2005 | Zanutto et al. |
| 2005/0282792 A1 | 12/2005 | Andres |
| 2006/0147383 A1 | 7/2006 | Mallard et al. |
| 2006/0188576 A1 | 8/2006 | Takuri |
| 2006/0228408 A1 | 10/2006 | Charman et al. |
| 2006/0239947 A1 | 10/2006 | Dias et al. |
| 2006/0292080 A1 | 12/2006 | Abram et al. |
| 2007/0041910 A1 | 2/2007 | Pitre et al. |
| 2007/0048369 A1* | 3/2007 | Foreman et al. ............ 424/464 |
| 2007/0059346 A1* | 3/2007 | Maibach ................ 424/443 |
| 2007/0190088 A1 | 8/2007 | Childs et al. |
| 2007/0207192 A1 | 9/2007 | Holl et al. |
| 2008/0207570 A1 | 8/2008 | Segura-Orsni |
| 2008/0234239 A1 | 9/2008 | Wheeler et al. |
| 2008/0254105 A1 | 10/2008 | Tapolsky et al. |
| 2010/0062975 A1 | 3/2010 | Houck |
| 2010/0279951 A1 | 11/2010 | Morgan et al. |
| 2013/0101525 A1 | 4/2013 | Buchta et al. |

FOREIGN PATENT DOCUMENTS

| | | | |
|---|---|---|---|
| EP | 0474517 A2 | 3/1992 | |
| EP | 0679154 A1 | 7/1994 | |
| EP | 0679392 A1 | 11/1995 | |
| EP | 0884995 A1 | 9/1997 | |
| EP | 0799620 | 10/1997 | |
| EP | 1039893 A1 | 10/2000 | |
| EP | 1178808 A1 | 11/2000 | |
| EP | 1641463 A1 | 12/2004 | |
| EP | 1686972 A1 | 6/2005 | |
| EP | 1575542 A1 | 9/2005 | |
| EP | 1758586 A1 | 12/2005 | |
| EP | 1758589 A1 | 12/2005 | |
| EP | 1771180 A1 | 12/2005 | |
| EP | 1758587 A1 | 1/2006 | |
| EP | 1758588 A1 | 1/2006 | |
| EP | 1758591 A1 | 1/2006 | |
| EP | 1765356 A1 | 1/2006 | |
| EP | 1778185 A1 | 1/2006 | |
| EP | 1970047 A1 | 3/2007 | |
| EP | 1970048 A1 | 3/2007 | |
| EP | 1970049 A1 | 3/2007 | |
| EP | 1331927 B1 | 12/2007 | |
| EP | 1970047 A1 | 9/2008 | |
| EP | 1970048 A1 | 9/2008 | |
| JP | 62135417 | 6/1987 | |
| JP | 2005325140 A | 11/2005 | |
| RU | 2238734 C2 | 10/2004 | |
| RU | 2276177 C2 | 9/2010 | |
| WO | WO 95/31211 A1 | 11/1995 | |
| WO | WO 96/25923 | 8/1996 | |
| WO | WO 97/32559 A1 | 9/1997 | |
| WO | WO99/55312 A2 | 11/1999 | |
| WO | WO 00/64450 A1 | 11/2000 | |
| WO | WO 01/62214 A1 | 8/2001 | |
| WO | WO0204570 A2 | 1/2002 | |
| WO | WO 02/34235 A1 | 5/2002 | |
| WO | WO 2004/041227 A1 | 5/2004 | |
| WO | WO 2005/001643 A2 | 1/2005 | |
| WO | WO 2005/011628 A2 | 2/2005 | |
| WO | WO 2005/011643 A1 | 2/2005 | |
| WO | WO 2005/016321 * | 2/2005 | ............ A61K 9/70 |
| WO | WO 2005/061321 * | 2/2005 | ............ A61K 9/70 |
| WO | WO 2005/082515 A2 | 9/2005 | |
| WO | WO 2006/050836 | 5/2006 | |
| WO | WO 2006/111426 A1 | 10/2006 | |
| WO | WO 2008/110815 A1 | 9/2008 | |
| WO | WO 2009/001099 A2 | 12/2008 | |
| WO | WO 2009/007409 | 1/2009 | |
| WO | WO 2009/071594 | 6/2009 | |
| WO | WO 2010/120838 A1 | 10/2010 | |
| WO | WO 2010/124096 | 10/2010 | |
| WO | WO 2010/141591 A1 | 12/2010 | |

OTHER PUBLICATIONS

EP 11158099.9 Search Report dated Sep. 20, 2011.
Chinese Patent Application No. 200880008496.X Office Action (with English translation) (11 pages).
EP Application No. 1196067.0 Ryttov Declaration (4 pages).
EP Application No. 11196069.6 Response filed Aug. 8, 2013 (93 pages).
Farines et al., "Analysis of the triglycerides of some vegetable oils," Journal of Chemical Education, 65(5):464-466 (1988).
Final Report on the safety assessment of peanut (Arachis hypogaea) oil etc. International Journal of Toxicology, 20(2):65-77 (2001).
Guenther et al., "Efficacy and safety of a new combination of calcipotriol and betamethasone dipropionate (once or twice daily) compared to calcipotriol (twice daily) in the treatment of psoriasis vulgaris: a randomized, double-blind, vehicle-controlled clinical trial," British Journal of Dermatology, 147:316-323 (2002).
JP 10-139669 A (1998) (English translation of claims)(2 pages).
Kaufmann et al., "A New Calciptriol/Betamethasone Dipropionate Formulation (DaivobetTM) is an Effective Once-Daily Treatment for Psoriasis vulgaris," Dermatology, 205:389-393 (2002).
Kim et al., "Lipolysis of Corn, peanut and randomized peanut oils," Lipids, 18(11):842-844 (1983).
Kragballe, "Treatment of psoriasis with calcipotriol and other vitamin D analogues," Journal of the American Academy of Dermatology, Dec. 1992, vol. 27, Issue 6, part 1 (Abstract only).
Kragballe et al., "Efficacy of once-daily treatment regimens wit calcipotriol/betamethasone dipropionate ointment and calcipotriol ointment in psoriasis vulgaris," British Journal of Dermatology, 150:1167-1173 (2004).
Lebwohl, "The Evolution of Vitamin D Analogues for the Treatment of Psoriasis," Arch. Dermatol., 131:1323-1324 (1995).
Ortonne et al., "Efficacy of treatment with calcipotriol/betamethasone dipropionate followed by calcipotriol alone compared with tacalcitol for the treatment of psoriasis vaulgaris: a randomized, doubl-blind trial," Dermatology, 2004209(4):308-313 (2004) PMID 15539894, Medline, DA Nov. 12, 2004.
PCT/EP2012/054498 International Search Report dated May 7, 2012.
PCT/GB2004/003329 International Search Report dated Feb. 16, 2005.
Poyner et al., "Long Term Treatment of Chronic Plaque Psoriasis with Calcipotriol" Journal of Dermatological Treatment, 4(4):173-177 1993.
Russian Patent Application No. 2009138045 Office Action (with English translation).
Sebba, "Preparation and Properties of Polyaphrons (Biliquid Foams)" Chemistry and Industry, Chemical Society, Letchworth, GB, No. 10, 1984, pp. 367-372.
Traulsen et al., "The Atrophogenic Potential and Dermal Tolerance of Calcipotriol/Betamethasone Dipropionate Ointment Compared with Betamethasone Dipropionate Ointment," Dermatology, 207: 166-172 (2003).
Van De Kerkhol et al., "A two-compound product containing calcipotriol and betamethasone dipropionate provides rapid, effective treatment of psoriasis vulgaris regardless of baseline disease severity", Dermatology, 210(4):294-299 (2005) (Abstract).
Van De Kerkhol et al., "Mixed treatment comparison of a two-compound formulation (TCF) product containing calcipotriol and betamethasone dipropionate with other topical treatments in psoriasis vulgaris," Current Medical Research & Opinion, 27(1):225-238 (2011).
Wheeler, "High Internal Phase Dispersions," Conference: Cosmetics and Coloids (online) Feb. 15, 2005, pp. 1-12.

(56) References Cited

OTHER PUBLICATIONS

U.S. Office Action cited in U.S. Appl. No. 12/076,248 mailed Jul. 27, 2015.
Decision of US Court of Appeals for Federal circuit, Leo Pharmaceutical Products, Ltd. Appelle, 2012-1520, Appeal from BPAI No. 95/000,153, decided Aug. 12, 2013.
Le Yan (Stability, Transport, and Applications of polyaphrons in porous media, A dissertation Submitted to the Graduate Faculty of the Louisianna State University and Agricultural and Mechanical College in Partial fulfillment of the Requirements for the degree of Doctor of Philosophy, May 2005).
Rathore et al.: An Insight into Ophthalmic Drug Delivery System; International Journal of Pharmaceutical Sciences and Drug Research, 2009, pp. 1-5.
Patel et al.: "Ophthalmic Drug Delivery System—A Review"; Der Pharmacia Lettre, 2010, 2, pp. 100-115, published Feb. 4, 2010.
Lye et al.: "Immobilization of Candida cylindracea Lipase on Colloidal Liquid Aphrons (CLAs) and Development of a Continuous CLA-Membrane Reactor"; Biotechnology and Bioengineering, vol. 51, pp. 69-78 (1996).
Stuckey et al.: The Immobilisation of Enzymes on Colloidal Liquid Aphrons (CLAs) for Bi-phasic Reactions: Stability, Protein Structure, and use in Crossflow Membrane Bioreactors (2000—estimated).

* cited by examiner

BIOERODIBLE PATCH COMPRISING A POLYAPHRON DISPERSION

This application is a US National Stage application of PCT International Patent Application No. PCT/GB2008/002197, filed 26 Jun. 2008, which claims benefit of U.S. Provisional Patent Application Ser. No. 60/929,394, filed 26 Jun. 2007, and Ser. No. 07252591.8, filed 26 Jun. 2007 in Europe, and which applications are incorporated herein by reference. To the extent appropriate, a claim of priority is made to each of the above disclosed applications.

The present invention relates to a bioerodible patch comprising a pharmaceutically active agent. The composition is designed to adhere to surfaces of mammals, and in particular to dermal and/or mucosal surfaces of mammals, and enables localized delivery of a pharmaceutically active agent to particular target site.

Bioadhesive carriers are known in the art and include gels, pastes, tablets and films. Commonly, mucoadhesive devices are in the form of a film or a patch which are designed to adhere upon application to a mucus membrane.

Recently, bioerodible devices have been developed having a bioadhesive layer and a non-bioadhesive layer. For example U.S. Pat. No. 5,800,832 discloses a water-soluble, bioerodible pharmaceutical delivery device for application to mucosal surfaces. The device comprises an adhesive layer and a non-adhesive backing layer. However, the delivery device of U.S. Pat. No. 5,800,832 has the disadvantage that the pharmaceutically active agent may be incompatible with the ingredients of the layers, which may result in precipitation of the active agent. In such a case the active agent cannot be uniformly distributed within the layers of the composition. Such incompatibilities can prevent entire classes of active agents being incorporated within the mucoadhesive device.

US 2003/0194420 A1 discloses a bioerodible, water-soluble carrier device comprising a non-bioadhesive backing layer, a bioadhesive layer and a composition comprising an active ingredient, wherein the composition is deposited onto a surface of either the non-bioadhesive backing layer or the bioadhesive layer after formation of the bioerodible, water-soluble, carrier device. Unlike U.S. Pat. No. 5,800,832, US 2003/0194420 A1 describes a process of preparing a mucoadhesive device which relies on depositing the active agent onto the surface of the device. One of the disadvantages of US 2003/0194420 A1 is that the active agent will not be uniformly distributed in the active-containing layer of the device and as a result will not allow controlled release.

There is a need to address at least some of the problems of pharmaceutical delivery agents of the prior art. In particular there is a need to develop a bioerodible patch which can deliver a wide variety of drugs, including those which are poorly water soluble.

Accordingly, there is provided a bioerodible patch comprising at least one bioadhesive layer and at least one non-bioadhesive layer, wherein the bioadhesive layer comprises at least one polyaphron dispersion and at least one bioadhesive polymer, and wherein the polyaphron dispersion comprises at least one pharmaceutically active agent.

According to another aspect of the present invention there is provided the use of the patch for treating illness, infections or diseases. In particular, according to another aspect of the present invention there is provided the use of the patch as described herein for treating depression, diabetes, drug addiction, epilepsy, fungal infection, gout, hypertension, malaria, migraines, Parkinson's disease, cancer, viral infections, bacterial infections, eczema, local or systemic pain, elevated cholesterol, inflammation, insomnia, protozoal infections, tapeworm infection, arrhymia, thrombosis, angina, allergic reaction, thyroid imbalance, psoriasis, water retention or gastro-intestinal infection.

According to another aspect of the present invention there is provided the use of the patch as described herein for the manufacture of a medicament for treating depression, diabetes, drug addiction, epilepsy, fungal infection, gout, hypertension, malaria, migraines, Parkinson's disease, cancer, viral infections, bacterial infections, eczema, local or systemic pain, elevated cholesterol, inflammation, insomnia, protozoal infections, tapeworm infection, arrhymia, thrombosis, angina, allergic reaction, thyroid imbalance, psoriasis, water retention or gastro-intestinal infection.

According to another aspect there is provided a method of making the patch as described herein comprising forming a polyaphron dispersion comprising a pharmaceutically active agent; mixing said polyaphron dispersion and a bioadhesive polymer to form the bioadhesive layer and providing on said bioadhesive layer a non-bioadhesive layer.

According to another aspect there is provided a method of making the patch as described herein comprising forming a non-bioadhesive layer; and providing on said non-bioadhesive layer a bioadhesive layer, wherein the bioadhesive layer comprises a polyaphron dispersion comprising a pharmaceutically active agent and a bioadhesive polymer.

By polyaphron dispersion as used herein is meant a particular kind of hydrophilic liquid-in-hydrophobic liquid or hydrophobic liquid-in-hydrophilic liquid dispersion comprising (a) a hydrophilic liquid miscible phase, (b) a second hydrophobic phase being immiscible or substantially immiscible with the first phase and (c) one or more surfactants, wherein the dispersed or discontinuous phase is in the form of small (e.g. micron to sub-micron diameter, but more usually at least 1 micron diameter) droplets, and the whole having the following characteristics, which distinguish polyaphron dispersions from conventional or common emulsions and other dispersion types:

1. They are capable of existing in a stable form wherein the volume fraction of the dispersed phase ($\phi_{ip}$) is greater than 0.7 and can be as high as 0.97. ($\phi_{ip}$ is the volume ratio of discontinuous to continuous phase expressed as a fraction).
2. The microscopic appearance of polyaphron dispersions where $\phi_{ip}$ is greater than 0.7 is that of an aggregate of individual droplets, pushed closely together into polyhedral shapes, resembling the appearance of a gas foam. In this form, the dispersion has gel-like properties and is referred to as a Gel Polyaphron Dispersion (GPD).
3. Stable polyaphron dispersions can be formed with a surfactant concentration less than 3% and more typically less than 2% by weight of the total composition.
4. Gel Polyaphron Dispersions (as described in 2 above) can be diluted to any extent by the addition of more continuous phase without the addition of more surfactant, when the gel-like properties disappear. Once $\phi_{ip}$ has been reduced to below 0.7, the individual droplets of internal phase become separated to take the form of spherical droplets, which remain stable and intact but which may nevertheless join together in loose associations and float to the top or sink to the bottom of the diluted dispersion (depending on the relative densities of the two phases). In this diluted form each droplet is referred to as a Colloidal Liquid Aphron (CLA). Simple shaking of the diluted dispersion instantly causes a homogeneous, stable dispersion of Colloidal Liquid Aphrons to re-form.

Each of the above characteristics and a combination of them clearly differentiate the polyaphron dispersions of the present invention from conventional emulsions and other dispersion types which do not have all of those characteristics. Polyaphron dispersions are disclosed in the following literature references by Sebba: "Biliquid Foams", J. Colloid and Interface Science, 40 (1972) 468-474 and "The Behaviour of Minute Oil proplets Encapsulated in a Water Film", Colloid Polymer Sciences, 257 (1979) 392-396, Hicks "Investigating the Generation, Characterisation, and Structure of Biliquid Foams", PhD Thesis, University of Bristol, 2005, Crutchley "The Encapsulation of Oils and Oil Soluble Substances Within Polymer Films", PhD Thesis, The University of Leeds, 2006 and Lye and Stuckey, Colloid and Surfaces, 131 (1998) 119-136. Aphrons are also disclosed in U.S. Pat. No. 4,486,333 and WO 97/32559.

Polyaphron dispersions are sometimes referred to as 'Biliquid Foams', 'High Internal Phase Emulsions (HIPEs)', 'High Internal Phase Ratio Emulsions (HIPREs)' and 'Gel Emulsions'. All such descriptions that refer to dispersions having the characteristics described above are polyaphron dispersions as used in the present invention.

Each aspect as described hereinbefore or hereinafter may be combined with any other aspect or aspects unless clearly indicated to the contrary. In particular any feature indicated as being preferred or advantageous may be combined with any other feature or features indicated as being preferred or advantageous.

The bioerodible patch of the present invention may be used in the localized treatment of body tissues, diseases, or wounds. It may be applied to the skin to allow transdermal delivery of the active agent.

The patch may be of particular use when applied to moist surfaces of mammals that are susceptible to bodily fluids, such as the mouth, or other types of mucosal surfaces. Mucosal surfaces include, but are not limited to corneal, conjunctival, nasal, buccal, sublingual, pulmonary, stomachic, intestinal, uteral, bladder, rectal and vaginal surfaces.

Upon application and adherence of the patch of the present invention to a surface, and preferably to a mucosal surface, the pharmaceutically active agent is delivered to the target site, the surrounding tissues, and other bodily fluids. The device preferably provides an appropriate residence time for effective drug delivery at the application site.

The present inventors have surprisingly found that at least some of the problems of compatibility (and uniform distribution) observed in the prior art between particular polymers and pharmaceutically active agents can be addressed. In particular, these problems may be addressed by formulating a bioadhesive layer comprising a bioadhesive polymer and a polyaphron dispersion, wherein the polyaphron dispersion comprises at least one pharmaceutically active agent. The polymer comprising the polyaphron dispersion may be formed into a single homogenous mass capable of being moulded into a desired shape. Such bioadhesive layers provide for the controlled release of the pharmaceutically active agent(s) over a specified period of time as the polymer dissolves and/or disintegrates. Because the polyaphron dispersion may be distributed throughout, and preferably distributed evenly throughout the bioadhesive layer, a substantially constant release profile of the pharmaceutically active agent may be achieved. Furthermore, the pharmaceutically active agent may be uniformly distributed throughout the bioadhesive layer in a solvated form. This is particularly advantageous for oil-soluble active agents, in which case the active agent may be dissolved in the oil phase of the polyaphron dispersion.

One advantage of the bioerodible patch of the present invention is that when the patch is in position, in for example the buccal cavity, the presence of the non-bioadhesive layer helps to direct the release of the pharmaceutically active agent through the mucosa. This reduces the inefficient loss of the active agent into the mouth, and therefore improves the efficiency of the drug delivery. Furthermore, as the pharmaceutically active agent may be present in a solvated form in the polyaphron dispersion good permeation into the mucosal membrane or skin or other bodily surface is achieved. Thus, the bioerodible patch of the present invention allows the delivery of a pharmaceutically active agent at a high concentration, at a specific location in an appropriate form to enable efficient uptake by the human/animal. Furthermore, as the pharmaceutically active agent may be dissolved in a suitable solvent it is possible to provide a patch comprising the pharmaceutically active agent at an appropriate concentration (for the specific use for which the patch is designed) for enhanced delivery to, for example, the mucous membrane.

A further advantage of the present invention is provided by the properties of polyaphron dispersions. In the present invention, the polyaphron dispersion is comprised within the bioerodible patch. When the bioerodible patch dissolves and/or disperses polyaphron dispersion droplets are released, and remain as individual droplets. The released polyaphron droplets are therefore capable of existing as discrete and separate entities with minimal risk of coalescence to produce larger droplets. Thus the discrete droplets maintain their high surface area through which the pharmaceutically active agent molecules may diffuse into or through the mucous membrane for local or systemic uptake. This is in contrast to, for example, emulsions wherein if an emulsion is entrapped within a polymer matrix, when the polymer matrix dissolves the emulsion tend to coalesce.

A further advantage of the present invention is that more than one polyaphron dispersion may be present in the patch. Each polypahon dispersion may comprise one or more pharmaceutically active agents, which may be present in the continuous or discontinous phase. This allows a patch to be provided which may encompass pharmaceutically active agents which are incompatible with one another using traditional delivery methods to be delivered to a target site in the same patch without detrimental stability issues.

The term "bioerodible patch" as used herein means that when the patch is in use in place on a human/animal surface, the components of the patch disperse and/or dissolve under the prevailing conditions such that the polyaphron dispersion, and hence the pharmaceutically active agent is released from the patch. This allows the patch to dissolve/disintegrate over a period of time, with natural body fluids slowly dissolving and eroding the away the patch. Additionally, or alternatively physical abrasion of the patch in place on a human/animal surface may aid the dispersion and/or dissolution of the patch. Unlike bandages, transdermal devices and other non-water soluble film systems, the user does not have to remove the patch following treatment.

Preferably, the patch is designed such that when it is placed in contact with water, or an aqueous environment (such as saliva, gastric juices, or plasma from open wounds) the patch disintegrates and/or dissolves, releasing the polyaphron dispersion and the pharmaceutically active agent.

Suitable polymers for use in the present invention may be water-dispersible and/or a water-soluble. Alternatively, or in addition, the polymer might undergo acid dissolution. The decomposition of the bioerodible patch may be a result of interaction of acidic/basic conditions and/or enzyme action with the polymers making up the patch. By careful selection of the polymer(s) in the bioadhesive/non-bioadhesive layers the rate of dispersion and/or dissolution of the layers may be controlled. This also allows the rate of release of the pharmaceutically active agent(s) to be varied.

Suitable periods of time for disintegration/dissolution will depend on the intended use of the patch. When the patch is designed for oral use, typically at least 50%, more preferably at least 60%, more preferably still at least 80% of the bioadhesive layer will disintegrate and/or dissolve within 20 minutes, more preferably within 10 minutes, more preferably still within 7 minutes of being in placed in the sublingual cavity. It will be understood that when the bioerodible patch is designed for dermal application, advantageously the rate of disintegration and/or dissolution of the bioadhesive layer will be much slower. For dermal use, the disintegration and/or dissolution of the bioadhesive layer may take from minutes to hours or days, depending on the choice of components.

The bioadhesive layer comprises a bioadhesive polymer. As used herein the term "bioadhesive polymer" refers to a polymer which adheres to a biological surface, such as a mucous membrane or skin tissue, preferably for an extended period of time.

Bioadhesive polymers are known in the art, for example in U.S. Pat. No. 5,474,768. Example 2 of U.S. Pat. No. 5,474,768 discloses a procedure for measuring the force required to separate two layers of freshly exercised rabbit stomach tissue that are adhered together by a bioadhesive polymer. Using the procedure defined in this example, a bioadhesive polymer can be defined as a material that requires a force of at least about 50 dynes/cm$^2$ to separate two adhered, freshly excised pieces of rabbit stomach tissue.

It will be understood that whilst the bioadhesive layer is designed to adhere to mucosal surfaces or skin tissue, the non-bioadhesive layer is designed so that it will not significantly adhere to such surfaces. Thus, when for example the bioerodible patch of the present invention is for sublingual use, the bioadhesive layer will adhere to the mucosal tissue in the sublingual area and will avoid detachment in normal use until the bioerosion (and drug delivery) has occurred. In this example, the non-bioadhesive layer will be sufficiently non-bioadhesive that it does not stick to the tongue, and will hence avoid competitive adhesion which may result in detachment of the patch.

Suitable bioadhesive polymers include polyacrylic acid, modified polyacrylic acid, sodium carboxymethyl cellulose, carboxymethyl cellulose, hydroxyethylcellulose, polyvinylpyrrolidone, cetylcellulose, hydroxypropylcellulose, hydroxypropylmethyl cellulose, polyvinyl alcohol, hydroxyethylmethyl cellulose, methylcellulose, hyaluronic acid, polysaccharides, pectin, chitosan, pullulan, tragacanth, sodium hyaluronate, gum arabica, modified starches, and Gantrez polymers (copolymers of methyl vinyl ether and maleic anhydride) and mixtures thereof. Preferably, the bioadhesive layer comprises polyvinyl alcohol. These polymers may be crosslinked. It will be understood that other bioadhesive polymers may be used in the present invention if they have suitable mucoadhesive and/or dermal adhesive properties.

The degree of bioadhesion will improve with molecular weight and with functionality (and in the case of polyvinyl alcohol with the degree of hydrolysis). One skilled in the art will know the grades of polymer to use for the purpose of bioadhesion.

It will be understood that the form of the polymer may influence the bioadhesion of the patch. If the polymer is partially hydrated prior to application at the point of use, typically the bioadhesion will be worse than if the polymer is dehydrated and then subsequently hydrated by the environment at the point of use. Subsequent hydration of the polymer may occur as a result of, for example, the interaction with the mucous membrane, saliva and/or blood.

The bioadhesive layer preferably comprises from 1 to 99% by weight of bioadhesive polymer, more preferably from 10 to 70% by weight, more preferably still from 40 to 60% by total weight of the bioadhesive layer.

The bioadhesive layer and/or the non-bioadhesive layer of the present invention may comprise a film forming polymer. Suitable film forming polymers are well known in the art and include, but are not limited to, cellulose acetate, cellulose acetate butyrate, polyvinylpyrrolidone, polyvinyl alcohol, maltodextrin, pullulan, modified starches, polyacrylic acid (high molecular weight), starch acetate, polyvinylpyrrolidone/polyvinylacetate copolymer, xantham gum, copolymers of lactic acid, caprolactone and glycolic acid and mixtures thereof. Cross-linked or plasticized film-forming polymers may be used to alter the dissolution kinetics of the layers.

The non-bioadhesive layer preferably comprises from 0 to 99% by weight of film forming polymer, more preferably from 0 to 30% by weight, more preferably still from 0 to 10% by total weight of the non-bioadhesive layer.

Other suitable polymers for use in the bioadhesive and/or non-bioadhesive layers are capable of undergoing a sol-gel transition by reason of temperature change (for example, gelatine) or by reason of crosslinking (for example the crosslinking of alginate salts by calcium ions) and include, for example, gelatine, pectins, agar agar, carrageens, alginates, other water dispersible or water soluble mouldable polymers known in the art. Mixtures of the above may also be used in the present invention. Preferred polymers include gelatine and carageenan gum. Most preferably, the polymer is gelatine.

Dried polymer powder may also be used in order to form the patch or to form part of the patch. Examples of suitable polymers in powder form include, but are not limited to, modified polyacrylic acid (for example, Noveon AA-1, Carbopol 974), gantrez polymers and carboxymethyl cellulose.

A plasticizer or a mixture thereof may be used in the present invention to make the bioerodible patch more elastic and pliable. Plasticizers may be selected from, for example, the group consisting of polyalcohol organic acids, hydroxyl acids, amines, acid amines, sulphoxides and pyrrolidones. In a preferred embodiment of the present invention the plasticizer is selected from the group of sorbitol, mannitol, glycerol, xylitol, maltitol (Maltisorb®), propylene glycol, polyethylene glycol, lactitol, trehalose, sorbitan esters and sorbitol anhydride and mixtures thereof.

The bioadhesive layer preferably comprises from 0 to 30% by weight of a plasticizer, more preferably from 5 to 20% by weight, more preferably still from 10 to 15% by weight, all percentages being based on the total weight of the bioadhesive layer.

The non-bioadhesive layer preferably comprises from 0 to 35% by weight of a plasticizer, more preferably from 5 to 20% by weight, more preferably still from 10 to 15% by weight, all percentages being based on the total weight of the non-bioadhesive layer.

It will be understood that the consistency of the layers of the patch may be varied from a gel-like consistency to a solid consistency by careful choice of ingredients.

It will be understood that the amount and choice of the plasticizer will help to determine the hardness of the final product. It may also effect the disintegration and/or dissolution of the moulded body, as well as its physical and chemical stability.

The polymers used in the layers of the present invention may be chosen such that they are sensitive to acidity or alkalinity so that the release of the entrapped pharmaceutically active agent(s) may be determined by a change of pH or by the presence of another chemical species.

The bioerodible patch of the present invention preferably comprises from 1 to 95% by weight of bioadhesive layer, more preferably from 10 to 40% by weight, more preferably still from 15 to 25% by weight of the total bioerodible patch.

The bioerodible patch of the present invention preferably comprises from 5 to 99% by weight of non-bioadhesive layer, more preferably from 60 to 90% by weight, more preferably still from 75 to 85% by weight of the total bioerodible patch.

It has surprisingly been found that the amount of polyaphron dispersion in the bioadhesive layer may be as high as 60% by weight of the total bioadhesive layer. Preferably, the amount of polyaphron dispersion in the bioadhesive layer is at least 20%, more preferably at least 30%, more preferably still at least 40% by weight of the total bioadhesive layer.

Preferably, the discontinuous phase of the polyaphron dispersion comprises a pharmaceutically acceptable oil phase. Examples of oils which may be used in the discontinuous phase of the aphrons include almond oil, babassu oil, blackcurrant seed oil, borage oil, canola oil, castor oil, coconut oil, cod liver oil, corn oil, cottonseed oil, evening primrose oil, fish oil, grapeseed oil, mustard seed oil, olive oil, palm kernel oil, palm oil, peanut oil, rapeseed oil, safflower oil, sesame oil, squalene, squalane, soybean oil, sunflower oil, walnut oil, wheat germ oil, hydrogenated castor oil, hydrogenated coconut oil, hydrogenated cottonseed oil, hydrogenated palm oil, hydrogenated soybean oil, partially hydrogenated soybean oil, hydrogenated vegetable oil, modified triglycerides, caprylic/capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl trilinoleate, glyceryl trilinolenate, glyceryl trioleate, glyceryl triundecanoate, linoleic glycerides, saturated polyglycolized glycerides, synthetic medium chain triglyceride containing primarily $C_8$-$C_{12}$ fatty acid chains, medium chain triglycerides, long chain triglycerides, modified triglycerides, fractionated triglycerides, and mixtures thereof.

Examples of mono and diglycerides which may be used in the present invention include propylene glycol mono and diesters having from 15 to 40 carbon atoms, including hydrolysed coconut oils (e.g. Capmul MCM), hydrolysed corn oil (e.g. Maisine 35-1).

The monoglycerides and diglycerides are mono- or di-saturated fatty acid esters of glycerol having eight to sixteen carbon chain length.

Essential oils may also be used in the present invention.

A suitable antioxidant may be added to the oil.

Preferably the bioadhesive layer comprises from 1 to 60% by weight of pharmaceutically acceptable oil, more preferably from 10 to 50% by weight, more preferably still from 20 to 40% by weight based on the total weight of the bioadhesive layer.

Preferably, the continuous hydrophilic phase of the polyaphron dispersion comprises water. The continuous hydrophilic phase may additionally comprise a co-solvent such as an aliphatic alcohol, polyethylene glycol, propylene glycol or glycerol, or mixtures thereof, and/or a gelling agent, thickening agent, rheology modifier and a stabiliser. Suitable gelling agents include alginate gums or their salts, guar gum, locust bean gum, xanthan gum, gum acacia, gelatin, hydroxymethyl-cellulose hydroxyethylcellulose, hydroxypropyl-cellulose, carboxymethylcellulose or its salts, bentonites, magnesium aluminium silicates, "Carbomers" (salts of cross-linked polymers of acrylic acid), or glyceryl polymethacrylates or their dispersions in glycols, or a polyvinylpyrrolidone polymer or a water-dispersible copolymer thereof, or any appropriate mixture of any of these polymers and gums.

Alternatively, the hydrophilic phase may be non-aqueous, or essentially non-aqueous. The hydrophilic phase may be, for example, an aliphatic alcohol, polyethylene glycol, propylene glycol or glycerol, or mixtures thereof.

The surfactants used in the present invention may be incorporated into either or both phases of the polyaphron dispersion(s). The surfactant used in the present invention is preferably an alkyl polyglycol ether, an alkyl polyglycol ester, an ethoxylated alcohol, a polyoxyethylene sorbitan fatty acid ester, a polyoxyethylene fatty acid ester, an ionic or non-ionic surfactant, a hydrogenated castor oil/polyoxyethylene glycol adducts containing from 25 to 60 ethoxy groups a castor oil/polyoxyethylene glycol adduct containing from 25 to 45 ethoxy groups, a sorbitan fatty acid ester (for example Span 20 or Span 80), a block copolymer of ethylene oxide and propylene oxide (for example Pluronic L121 or Pluronic F68), or a mixture thereof.

It will be understood that other suitable surfactants may be used.

Preferably the bioerodible patch of the present invention comprise less than 5% by weight of surfactant, more preferably less than 2% by weight, more preferably still less than 1% by weight of the bioerodible patch.

The pharmaceutically active agent may be substantially present in either the continuous or the discontinuous phase of the polyaphron dispersion. Alternatively, the pharmaceutically active agent may be substantially present in both the continuous and the discontinuous phase. This will in part be determined by the solubility of the pharmaceutically active agent in a specific phase.

Preferably the bioadhesive layer comprises from 0.0001 to 60% by weight of pharmaceutically active agent, more preferably from 0.1 to 50% by weight, more preferably still from 1 to 30% by weight based on the total weight of the bioerodible patch. However, it will be understood that the preferred amount of pharmaceutically active agent will depend on a number of factors. For example, it will depend on the proposed method of application of the patch, i.e. dermal or sublingual, on the specific pharmaceutically active agent used, the solubility of the active agent and the purpose of the treatment.

Where the pharmaceutically active agent is a "poorly water soluble drug", preferably it is dissolved in the oil phase of the polyaphron dispersion. As used herein the term poorly water soluble is meant a drug which will dissolve in water in an amount of less than 1% by weight. In this embodiment it may be advantageous to use a co-emulsifier in the formation of the polyaphron dispersion in an amount sufficient to complete the solubilization of the poorly water-soluble drug. A suitable co-emulsifier is a phosphoglyceride, a phospholipid, for example lecithin, or a free fatty acid that is liquid at room temperature, for example iso-stearic acid, oleic acid, linoleic acid or linolenic acid.

The pharmaceutically active agent may, for example, be selected from an analgesic or anti-inflammatory agent, an anthelmintic, an anti-arrhythmic agent, an anti-coagulant, an anti-depressant, an anti-diabetic agent, an anti-epileptic agent, an anti-fungal agent, an anti-gout agent, an anti-hypertension agent, an anti-malarial, an anti-migraine agent, an anti-muscarinic agent, an anti-neoplastic agent, an anti-protozoal agent, an anti-thyroid agent, an anxiolytic, sedative, hypnotic or neuroleptic agent, a corticosteroid, a diuretic, an anti-Parkinsonian agent, a gastro-intestinal agent, a histamine H1-receptor antagonist, a lipid regulating agent, an anti-anginal agent, a thyroid agent, a nutritional agent, an antipyretic agent, an antibacterial agent, an immunosuppressant, an antiviral agent, hypothalmic or pituitary hormones, sex hormones, prostaglandins, vaccines, cough suppresants, local anaesthetics, immuno-globulins and antisera, an opioid analgesic, a stimulant, a viral vector for gene therapy or a therapeutic mixture thereof.

Preferably the stimulant is nicotine.

Examples of pharmaceutically active agents which may be used in the present invention include the following:

Analgesics and anti-inflammatory agents: aceclofenac, aloxiprin, auranofin, azapropazone, buprenorphine, benorylate, capsaicin, celecoxib, diflunisal, etodolac, fenbufen, fenoprofen calcium, flurbiprofen, ibuprofen, ibuproxam, indomethacin, ketoprofen, lornoxicam, meclofamate, mefenamic acid, meloxicam, nabumetone, naproxen, nimesulide, oxyphenbutazone, phenylbutazone, piroxicam, refocoxib, sulindac, suxibuzone, tolmetin, zileuton.

Anthelmintics: albendazole, bephenium hydroxynaphthoate, dichlorophen, ivermectin, mebendazole, oxfendazole, oxantel, praziquantel, pyrantel, thiabendazole.

Anti-arrhythmic agents: amiodarone, disopyramide, quinidine sulphate.

Anti-bacterial agents: benethamine penicillin, cinoxacin, ciprofloxacin, clarithromycin, clofazimine, cloxacillin, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim, cefrozil, fusidic acid, muciprocin, nifuroxazide, oxacillin, sparfloxacin, sulphadoxin, telithromycin, trovafloxacin.

Anti-coagulants: dicoumarol, dipyridamole, nicoumalone, phenindione, clopidogrel, tirofibran.

Anti-depressants: amoxapine, maprotiline, trimipramine, paroxetine, sertraline.

Anti-diabetics: acetohexamide, chlorpropamide, glibenclamide, gliclazide, glipizide, tolazamide, insulin, tolbutamide, rasiglitazone, pioglitazone, andglimepiride.

Anti-epileptics: beclamide, carbamazepine, clonazepam, ethotoin, methoin, methsuximide, methylphenobarbitone, phenacemide, phenobarbitone, phenyloin, phensuximide, primidone, sulthiame, valproic acid, and tiagabine.

Anti-fungal agents: azithromycin, oxiconazole, tolnaftate, voriconazole, amphotericin, butoconazole nitrate, clotrimazole, econazole nitrate, fluconazole, griseofulvin, itraconazole, ketoconazole, miconazole, natamycin, sulconazole nitrate, terbinafine, terconazole, tioconazole, undecenoic acid.

Anti-gout agents: allopurinol, probenecid, sulphin-pyrazone.

Anti-hypertensive agents: amlodipine, benidipine, candesartan cilexitil, clonidine, darodipine, diazoxide, eprosartan, felodipine, irbesartan, irinotecan, isradipine, losartan, minoxidil, nicardipine, nifedipine, nimodipine, prazosin, raubasine, reserpine, tamsulosin, telmisartan, valsartan.

Anti-malarials: amodiaquine, chloroquine, halofantrine, mefloquine, proguanil, pyrimethamine, quinine sulphate.

Anti-migraine agents: dihydroergotamine mesylate, ergotamine, methysergide, pizotifen, alpiropride, eletriptan, frovatriptan, lisuride, naratriptan, rizatriptan, sumatriptan, zolmitriptan.

Anti-muscarinic agents: atropine, benzhexyl, biperiden, hyoscyamine, mepenzolate bromide, tropicamide.

Anti-neoplastic agents and immunosuppressants: aminoglutethimide, amsacrine, anastrazole, azathioprine, bicalutamide, busulphan, chlorambucil, clobetasol, cyclosporine, dacarbazine, estramustine, etoposide, exemestane, gefitinib, letrozole, lomustine, melphalan, mercaptopurine, methotrexate, mitomycin, mitotane, mitozantrone, mycophenolate mofetil, nilutanide, paclitaxel, procarbazine, sirolimus, tacrolimus, tamoxifen, testolactone, toremifine.

Anti-protazoal agents: clioquinol, diiodohydroxyquinoline, diloxanide, dinitolmide, furzolidone, metronidazole, nitrofurazone, tinidazole, atovaquone, ornidazole.

Anti-thyroid agents: carbimazole, propylthiouracil.

Anti-viral agents: adefovir dipovoxil, amprenavir, efavirenz, lopinavir, nelfinavir, penciclovir, ritonavir, saquinavir, tipranavir.

Anxiolytic, sedatives, hypnotics and neuroleptics: aripiprazole, eszopaclone, paroxetine, sertindole, zaleplon, zolpidem, alprazolam, amylobarbitone, barbitone, bromazepam, bromperidol, brotizolam, butobarbitone, carbromal, chlordiazepoxide, chlormethiazole, chlorpromazine, clobazam, clozapine, diazepam, droperidol, ethinamate, fluanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone.

β-Blockers: nadolol, pindolol.

Bronchodilators and anti-asthma agents: zafirlukast, zileuton.

Cardiac Inotropic agents: digitoxin, digoxin, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone, clobetasol, clobetasone, desonide, mometasone, rimexocone.

Diuretics: acetazolamide, amiloride, bendrofluazide, bumetanide, chlorothiazide, chlorthalidone, ethacrynic acid, frusemide, metolazone, spironolactone, triamterene.

Anti-parkinsonian agents: bromocriptine, apomorphine selegiline.

Erectile dysfunction agents: sildenafil, vardenifil, tadalafil.

Gastro-intestinal agents: bisacodyl, cimetidine, diphenoxylate, domperidone, famotidine, loperamide, droperidol, dronabinol, nabilone, palonosetron, granisetron, ondansetron, pizotifen, mesalazine, omeprazole, sulphasalazine.

Antihistamines: cinnarizine, cyclizine, cyproheptadine, dimenhydrinate, meclozine, oxatomide, terfenadine, acrivastine, antazoline, azatadine, azelastine, bramazine (bromodiphenhydramine), brompheniramine, buclizine, carbinoxamine, cabastin, carebastine, cetirizine, chlorcyclizine, chlorphenamine (chlorpheniramine), chlorphenoxamine, chloropyrilene, cinnarizine, clemastine, clocinizine, cyclizine, cyproheptadine, deptropine, desloratidine, diphenylhydramine, dimenhydrinate, diphenylpyraline, doxylamine, ebastine, embramine, emedastine, epinastine, fexofenadine, flunarizine, halopyramine, histapyrrodine, homochlorcyclizine, hydroxyzine, isothipendyl, levocabastine, loratadine, mebhydrolin, meclozine, mefenidramium, mepyramine, mequitazine, methdilazine, mizolastine, oloptadine, oxatomide, oxomemazine, phenindamine, pheniramine, phenyltoloxamine, pimethixene, promethazine, promethazine, propiomazine, pyrrobutamine, rupatadine, setastine, talastine, temelastine, terfenadine, thiethylperazine, trimethobenzamide, tripelennamine, triprolidine, tritoqualine.

Lipid regulating agents: bezafibrate, clofibrate, lovastatin, pravastatin, rosuvastatin, simvastin, fenofibrate, gemfibrozil, probucol.

Nitrates and other anti-anginal, agents: amyl nitrate, glyceryl trinitrate, isosorbide dinitrate, pentaerythritol tetranitrate.

Nutritional agents: betacarotene, vitamin A, vitamin B2, vitamin D, vitamin E, vitamin K, vitamin B12.

Opioid analgesics: codeine, dextropropyoxyphene, diamorphine, dihydrocodeine, meptazinol, morphine, pentazocine, fentanyl.

Sex hormones: clomiphene, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone.

Stimulants: dexamphetamine, dexfenfluramine, mazindol, nicotine.

The viral vector may be a retrovirus (such as Moloney murine leukaemia virus), a lentivirus, an adenovirus, an adeno-associated virus (AAV) or a nanoengineered substance such as Ormosil.

The active agent may be a monoclonal antibody.

Pharmaceutically acceptable salts, isomers and derivatives thereof may be substituted for these drugs. Suitable pharmaceutical salts include, for example, hydrochloride, maleate, tartrate, embonate. Mixtures of pharmaceutically active agents may be used where therapeutically effective.

The bioerodible patch of the present invention is preferably presented in a unit dosage form. Each patch dosage may comprise from 0.05 mg to 500 mg, and in particular from 0.1 mg to 20 mg of the pharmaceutically active agent. It will be understood that the preferred unit dosage will depend on the particular pharmaceutically active agent used and the intended method of application of the patch.

Wherein the patch is a buccal or sublingual patch, a variety of flavouring agents may also be added. Any suitable amount and type of artificial and/or natural flavouring agents can be used in any sensorially acceptable fashion. For example, the flavour can constitute 0.1% to 20% by weight of the total weight of the patch, preferably 0.5% to 5% by weight. The flavouring agents can include, for example, essential oils, synthetic flavours or mixtures, including but not limited to, oils delivered from plants and fruits such as citrus oils, fruit essences, peppermint oil, spearmint oil, other mint oils, clove oils, oil of wintergreen, anise and the like, flavour components with germ killing properties such as menthol, eucalyptol, thymol, and combinations thereof.

Colouring agents may be included in the patch. These may include, for example, natural food colors and dyes suitable for drug applications, and may be present in amounts from 0.01% to 1.5% by weight of the total patch.

In a preferred embodiment the non-bioadhesive layer comprises a flavouring agent and/or a colouring agent.

In another embodiment the non-bioadhesive layer comprises at least one polyaphron dispersion. The polyaphron dispersion may comprise a flavouring agent, a colouring agent, a taste-masking composition and/or a fragrance or odour neutralising/masking component.

The patch of the present invention may comprise an opacifer, or a mixture of opacifers. The opacifer may be added in order to obtain an opaque patch or in order to protect light sensitive pharmaceutically active agents dispersed within said patch. Opacifers may be present in an amount of from 0.01% to 5% by weight, preferably 0.1% to 3% by weight of the total weight of the patch and may be selected from the group of titanium dioxide, calacium carbonate, iron oxide and bentonite clay and talc. Preferably the opacifer is titanium dioxide.

The patch may comprise disintegrants, fillers and bulking materials. Salt and other low molecular weight highly soluble materials may also be included to aid dissolution. In addition and/or alternatively, the presence of salts may influence the osmotic process and stabilisation of the patch. The presence of bulking materials and fillers in the patch may be useful in aiding the processing and manufacture of the patch (for example speeding up drying). Furthermore, they may assist the final dissolution and the performance of the patch. The patch may comprise from 0.1 to 40% by weight of bulking materials and/or fillers based on the total dry weight of the patch, preferably from 5 to 30% and more preferably from 15 to 25% by weight.

Examples of suitable bulking materials and fillers are calcium carbonate, pigments, fumed silicas, microcrystalline cellulose, calcium phosphate, magnesium aluminium silicate and bentonite and kaolin clays.

In one embodiment of the present invention the pharmaceutically active agent is nicotine, and the non-bioadhesive layer comprises a flavouring agent.

In one embodiment of the present invention the bioerodible patch is a sublingual patch, comprising a bioadhesive layer and a non-bioadhesive layer, wherein the bioadhesive layer comprises a polyaphron dispersion and a bioadhesive polymer, and wherein the polyaphron dispersion comprises a pharmaceutically active agent. Preferably the pharmaceutically active agent is nicotine. In this embodiment, preferably the non-bioadhesive polymer comprises gelatine, and a flavouring agent. Preferably the bioadhesive layer comprises polyvinyl alcohol and/or polyvinylpyrrolidone. In place in the mouth, the bioadhesive layer adheres to the floor of the sublingual cavity such that the non-bioadhesive may contact the underside of the tongue of the user. This embodiment has several advantages. In particular, the formulation of this embodiment provides a strong, flexible and comfortable patch. Furthermore, the flavouring agent present in the non-bioadhesive layer provides a taste masking function. This may be of particular use when the pharmaceutically active agent has an unpleasant taste, for example, nicotine.

It will be understood that by careful choice of the polymers used in the bioadhesive and non-bioadhesive layers the bioerodible patch may be designed such that either the bioadhesive or the non-bioadhesive layer dissolves and/or disperses at a faster rate that the other layer. For example, wherein the patch is a sublingual patch, it is preferable, when the non-bioadhesive layer comprises a tasking masking or flavouring agent, for the non-bioadhesive layer to dissolve and/or disperse at a slower rate than the bioadhesive layer.

The bioerodible patch may comprise more than one bioadhesive and/or non-bioadhesive layers.

The size and shape of the bioerodible patch will be determined by the desired use of said patch, for example, for dissolving in the mouth, or for applying to an open wound or inserting into the rectum or vagina as required. Suitable shapes include disks, ellipses, squares, rectangles and parallepipedes. The surface area of the non-bioadhesive layer is preferably larger than the surface area of the bioadhesive layer.

Wherein the bioadhesive and non-bioadhesive layers are films, the thickness of the device may vary, depending on the thickness of each of the layers. Preferably the bilayer thickness ranges from 0.05 to 3 mm, and more preferably from 0.2 to 2 mm and even most preferably between 0.3 and 1.5. The thickness of each layer may vary from 10 to 99% of the overall thickness of the device, and preferably varies form 30 to 60%.

The bioerodible patch as described herein may further comprise at least one peelable sheet which may be provided on either or both the bioadhesive layer and/or the non-bioadhesive layer. For ease of handling and for convenience preferably a peelable sheet is provided at least on the bioadhesive layer. Suitable materials for said peelable sheet will be well known in the art and include, but are not limited to, for example, polyethylene, polyethleneterephthalate, polypropylene, polystyrene, polyvinylchloride, and polyvinyl acetate.

The bioerodible patch of the present invention may be provided in an airtight packaging system in order to prevent deterioration. Suitable systems are known in the art.

One advantage of the bioerodible patch for use in buccal or sublingual delivery is that, unlike absorption from the gut, the pharmaceutically active agent enters the systematic circulation from the buccal cavity at a point where the blood does not immediately go through the liver (where much of it is metabolised before it can perform its desired effect). Avoidance of heptatic metabolism dramatically improves the bioavailablity of the pharmaceutically active agent. Unlike other buccal delivery dosage forms, such as dry films, quick dissolving tablets, lozenges and the like, the patch of the present invention has the advantage that the bioadhesive and non-bioadhesive layers may be formulated to be soft, pliable and comfortable to use whilst having a relatively high concentration of pharmaceutically active agent, and in particular oil-soluble pharmaceutically active agent, for release in a readily absorbed form. Many of the buccal delivery dosage forms known in the art are not suitable for delivering poorly water soluble drugs. As the patch of the present invention may be held in place by the bioadhesive layer, advantageously the pharmaceutically active agent will generally not be lost by swallowing, thus a more consistent dose is provided.

In one embodiment of the present invention the bioerodible patch comprises a bioadhesive layer, wherein the bioadhesive layer comprises a first polyaphron dispersion comprising a first pharmaceutically active agent and a further second polyaphron dispersion comprising a further second pharmaceutically active agent. The first and second pharmaceutically active agent may be the same or different. In this embodiment the pharmaceutically active agents may be, for example, nadolol and lorazepam (for anxiety), azelastine and ketoprofen (for antihistamine and pain), simvastatin and ezetimbe (statin in combination with a cholesterol absorption inhibitor).

In one embodiment of the present invention there is provided a wound dressing comprising the bioerodible patch as described herein.

In another embodiment of the present invention there is provided a bioerodible capsule comprising the bioerodible patch as described herein. Suitable materials for making a bioerodible capsule are well known in the art and include, for example, HPMC (hydroxypropylmethyl cellulose) with an enteric coating such as cellulose acetate phthalate. As the capsule travels through the intestinal system of a patient, the capsule will act as a protective covering for the patch, until the capsule is located at the desired position. The capsule is then designed to dissolve, degrade or disintegrate to enable the patch to adhere to the mucous membrane and deliver the pharmaceutically active agent as it dissolves, degrades or disintegrates.

According to the present invention there is provided a method of making the patch as defined herein comprising forming a polyaphron dispersion comprising a pharmaceutically active agent; mixing said polyaphron dispersion and a bioadhesive polymer to form the bioadhesive layer and providing on said bioadhesive layer a non-bioadhesive layer.

The bioadhesive layer may be formed by printing the bioadhesive polymer onto either a temporary surface or onto a pre-existing layer.

In another aspect there is provided a method of making the bioerodible patch as described herein comprising forming a non-bioadhesive layer; and providing on said non-bioadhesive layer a bioadhesive layer, wherein the bioadhesive layer comprises a polyaphron dispersion comprising a pharmaceutically active agent and a bioadhesive polymer.

The non-bioadhesive layer may be formed by printing the non-bioadhesive polymer onto either a temporary surface or onto a pre-existing layer.

In one embodiment when the bioadhesive layer comprises a bioadhesive film forming polymer comprising a polyaphron dispersion, the bioadhesive layer may be formed by casting the film forming polymer and allowing it to dry. When the film is dry the non-bioadhesive layer may be provided on the bioadhesive layer and allowed to dry (if the non-bioadhesive layer comprises a film-forming polymer), or allowed to go through a sol gel transition (if, for example, gelatine is used).

The layers may be dried, partially dried, or may be wet before application of the second layer.

The bioadhesive and/or non-bioadhesive layer may be formed by techniques known in the art such as by printing, film dipping, film coating, film casting, spin coating or by spraying followed by drying. The coating solution may be applied using a variety of methods including doctor blade, extrusion, roller, spraying, brush painting or wiping. The layer may be produced on an appropriate support such as a temporary surface or onto a pre-existing layer. The solution may be applied at the desired thickness and dried (if required) using either an oven or preferably a flow of heated gas (such as air). The temporary surface may be a polymer-coated paper, Mylar or any other appropriate non-deformable and impervious substrate. Preferably the surface holds the film dimensionally stable during coating and setting/drying processes but allows the resulting layer/patch to be released (for example by peeling) when required. It may be desirable to cut the film on this substrate to the appropriate desired geometry and then detach the resulting product. The solids content of the coating solution, the resulting solution viscosity and coating thickness applied determine the amount of coating film to be deposited on the casting surface.

In the method of making the bioerodible patch as defined herein appropriate steps may be taken in order to avoid or reduce any degradation or loss of the pharmaceutical agent. One skilled in the art will be aware of appropriate steps that may be taken. These may include control of temperature, atmosphere, contaminants and light. For example the method of making the patch may require low temperature drying in an inert flowing gas with appropriate filtration and in a darkened environment in order to avoid decomposition or contamination of the pharmaceutical agent. Other specific factors may also need to be addressed which would be obvious to one skilled in the art.

Powdered polymers may be incorporated into the patch either by addition onto another wet (or partially wet) polymer layer or onto a fully dried tacky layer. In the case of the "wet" format the excess water helps to hydrate the polymer causing it to be fixed onto the existing polymer layer. The level of water present is not usually enough to fully hydrate/dissolve the powdered polymer, only sufficient to make it adhere. The system is subsequently dried further. In the case of the "tacky" system a highly plasticised base layer is cast and dried fully. The powder is then applied in excess to this layer and a certain proportion sticks to the base layer due to that layers inherent tackiness.

An additional compatibilising (bridging) polymer may be provided between the bioadhesive and the non-bioadhesive layer. The additional compatibilising (bridging) polymer binds the bioadhesive and the non-bioadhesive layer together to prevent, or substantially prevent, separation in use.

In one embodiment of the present invention there is provided a method for administering the bioerodible patch as described herein to a human or animal, comprising applying the bioerodible patch as described herein to a mucosal surface of the human or animal. Mucosal surfaces include, but are not limited to corneal, conjunctival, nasal, buccal, sublingual, pulmonary, gastric, intestinal, uteral, bladder, rectal and vaginal surfaces. This method may be used for the treatment of depression, drug addiction, diabetes, epilepsy, fungal infection, gout, hypertension, malaria, migraines, Parkinson's disease, cancer, viral infections, bacterial infections, eczema, local or systemic pain, elevated cholesterol, inflammation, insomnia, protozoal infections, tapeworm infection, arrhymia, thrombosis, angina, allergic reaction, thyroid imbalance, psoriasis, water retention or gastro-intestinal infection. The bioerodible patch may be located locally on a mucousal surface of a patient/mammal for example, by hand or during surgery. Alternatively, or additionally, the bioerodible patch may be located on a mucosal surface of a patient/mammal indirectly, for example, by enclosing the patch of the present invention in a capsule suitable for oral administration.

In another embodiment of the present invention there is provided a kit of parts comprising:
(i) at least one bioadhesive layer which comprises at least one polyaphron dispersion comprising a pharmaceutically active agent and at least one bioadhesive polymer; and
(ii) and at least one non-bioadhesive layer.

The following Examples further illustrate the present invention.

Polyaphron Preparation

A suitable vessel is charged with the aqueous phase of the polyaphron dispersion. The oil phase was added at a constant rate with stirring, using a sweep stirrer or an orbital mixer. After completion of the oil addition, the stirring was continued until the size of the oil droplets became stable or reached a desired size.

| Polyaphron dispersion 1 | % (w/w) | Weight (g) |
|---|---|---|
| Oil phase | | |
| Soya bean oil | 71.7 | 21.51 |
| Cremophor RH 40 (BASF) | 1.0 | 0.3 |
| Nicotine | 17.3 | 5.19 |
| Aqueous phase | | |
| Poloxamer 188 (10 w/w %) (BASF) in Demin water | 8.2 | 2.46 |
| Nicotine | 1.8 | 0.54 |
| | 100 | 30 |

| Polyaphron dispersion 2 | % (w/w) | Weight (g) |
|---|---|---|
| Oil phase | | |
| Soya bean oil | 79.9 | 23.97 |
| Cremophor RH 40 (BASF) | 1.0 | 0.3 |
| Nicotine | 9.1 | 2.73 |
| Aqueous phase | | |
| Poloxamer 188 (10 w/w %) (BASF) in Demin water | 9.1 | 2.73 |
| Nicotine | 0.9 | 0.27 |
| | 100 | 30 |

| Polyaphron dispersion 3 | % (w/w) | Weight (g) |
|---|---|---|
| Oil phase | | |
| Soya bean oil | 88.5 | 53.4 |
| Vitamin E Acetate | 0.5 | 0.3 |
| Span 80 | 1.0 | 0.6 |
| Aqueous phase | | |
| Poloxamer 188 (10 w/w %) in Demin water | 10.0 | 6.0 |
| | 100 | 60.0 |

| Polyaphron dispersion 4 | % (w/w) | Weight (g) |
|---|---|---|
| Oil phase | | |
| Waglinol 3/9280 | 78.5 | 23.55 |
| Lime flavour 051.182/T | 10.0 | 3.0 |
| Oleth 10 | 0.75 | 0.225 |
| Etocas 29 | 0.75 | 0.225 |
| Aqueous phase | | |
| Poloxamer 188 (10 w/w %) in Demin water | 10.0 | 3.0 |
| | 100 | 30 |

| Polyaphron dispersion 5 | % (w/w) | Weight (g) |
|---|---|---|
| Oil phase | | |
| Soybean oil | 83.55 | 25.06 |
| Nicotine | 5.55 | 1.67 |
| Sorbitan monooleate | 0.90 | 0.27 |

| Polyaphron dispersion 5 | % (w/w) | Weight (g) |
|---|---|---|
| Aqueous phase | | |
| Poloxamer 188 (10 w/w %) in Demin water | 10.0 | 3.0 |
| | 100 | 30 |

| Polyaphron dispersion 6 | % (w/w) | Weight (g) |
|---|---|---|
| Oil phase | | |
| Ibuprofen | 6.6 | 0.66 |
| (−)Menthol | 2.2 | 0.22 |
| 501500T Mint Flavour | 8.90 | 0.89 |
| Cremophor RH 40 | 0.90 | 0.09 |
| Span 80 | 0.60 | 0.06 |
| Olive Oil | 80.80 | 8.08 |
| Aqueous phase | | |
| Poloxamer 188 (10 w/w %) in Demin water | 10.0 | 1.00 |
| | 100 | 10.00 |

Preparation of the Bioadhesive Layer

Using a suitable vessel the components of the bioadhesive layers are mixed under low shear conditions. Bioadhesive solutions 4 and 5 were heated to 80 degrees centigrade to facilitate the dissolution of the poly(vinylalcohol).

Bioadhesive layer 4 was exposed to high shear (2000 rpm) mixing to ensure adequate distribution of the pigment particles.

Bioadhesive layer 6 was made by heating to 55 degrees centigrade with low shear stirring. The system was kept at this temperature until used.

| Bioadhesive layer 1 | % (w/w) | Weight (g) |
|---|---|---|
| Polyvinyl alcohol solution in demin water (20% w/w) | 87.3 | 10 |
| Polyaphron dispersion 1 | 8.4 | 0.96 |
| Glycerine | 4.3 | 0.50 |
| | 100 | 11.46 |

| Bioadhesive layer 2 | % (w/w) | Weight (g) |
|---|---|---|
| Polyvinyl alcohol solution in demin water (20% w/w) | 87.3 | 10 |
| Polyaphron dispersion 2 | 8.4 | 0.96 |
| Glycerine | 4.3 | 0.50 |
| | 100 | 11.46 |

| Bioadhesive layer 3 | % (w/w) | Weight (g) |
|---|---|---|
| Polyvinyl alcohol solution in demin water (20% w/w) | 91.30 | 91.30 |
| Polyaphron dispersion 3 | 8.70 | 8.70 |
| | 100 | 100 |

| Bioadhesive layer 4 | % (w/w) | Weight (g) |
|---|---|---|
| Water | 50.83 | 15.25 |
| Poly(vinylalcohol) (Gohsenol EG-05, Nippon Gohsei) | 15.73 | 4.72 |
| Titanium dioxide (C47-060, Suncroma) | 3.48 | 1.04 |
| Sorbitol | 9.43 | 2.83 |
| Sodium chloride | 4.71 | 1.41 |
| Polyaphron dispersion 5 | 15.82 | 4.75 |
| | 100.00 | 30.00 |

| Bioadhesive layer 5 | % (w/w) | Weight (g) |
|---|---|---|
| Poly(vinylpyrrolidone) (Polyplasdone K32, ISP) | 32.35 | 9.71 |
| Sodium chloride | 1.80 | 0.54 |
| Sorbitol | 13.88 | 4.16 |
| Poly(vinylalcohol) (Gohsenol EG-05) | 5.32 | 1.60 |
| Water | 21.24 | 6.37 |
| Polyaphron Dispersion 6 | 25.41 | 7.62 |
| | 100.00 | 30.00 |

| Bioadhesive layer 6 | | |
|---|---|---|
| Poly (vinyl pyrrolidone) K90 | 10.0 | 5.0 |
| Xylitol | 5.0 | 2.5 |
| Gelatine | 20.0 | 10.0 |
| Water | 56.00 | 28.00 |
| Food dye | 0.25 | 0.12 |
| Poly aphron dispersion 6 | 8.75 | 4.38 |
| | 100 | 50.0 |

Preparation of Non-bioadhesive Polymer Solutions

Non-bioadhesive polymer solutions 1 to 5 was dissolved and mixed with low shear stirring at 50 degree centigrade until a homogeneous mixture was produced.

Non-bioadhesive polymer solution 6 was mixed with low shear stirring at 85 degree centigrade until a homogeneous mixture was produced. All solutions were kept at elevated temperatures until used.

| Non-bioadhesive polymer solution 1 | % (w/w) | Weight (g) |
|---|---|---|
| Gelatine GP grade | 30 | 30 |
| Demin water | 55 | 55 |
| Glycerine | 15 | 15 |
| | 100 | 100 |

| Non-bioadhesive polymer solution 2 | % (w/w) | Weight (g) |
|---|---|---|
| Polyaphron Dispersion 3 | 10 | 1 |
| Non-bioadhesive polymer solution 1 | 90 | 9 |
| | 100 | 10 |

| Non-bioadhesive polymer solution 3 | % (w/w) | Weight (g) |
|---|---|---|
| Polyaphron Dispersion 4 | 10 | 1 |
| Non-bioadhesive polymer solution 1 | 90 | 9 |
| | 100 | 10 |

| Non-bioadhesive polymer solution 4 | % (w/w) | Weight (g) |
|---|---|---|
| Gelatine | 28.24 | 3.53 |
| Sorbitol | 20.00 | 2.50 |
| Water | 51.76 | 6.47 |
| | 100.00 | 12.5 |

| Non-bioadhesive polymer solution 5 | % (w/w) | Weight (g) |
|---|---|---|
| Gelatine | 24.53 | 21.18 |
| Sorbitol | 24.53 | 21.18 |
| Microcrystaline cellulose (Chemfields PH101) | 5.79 | 5.00 |
| Blue food dye | 0.17 | 0.15 |
| Sodium metabisulfite | 0.03 | 0.03 |
| Water | 44.95 | 38.82 |
| | 100.00 | 86.36 |

| Non-bioadhesive solution 6 | | |
|---|---|---|
| k-carrageenan | 2.0 | 0.8 |
| Microcrystalline cellulose | 15.0 | 6.0 |
| Xylitol | 5.0 | 2.0 |
| Water | 78.0 | 31.2 |
| | 100 | 40.0 |

Supplementary Layers

All supplementary layers were mixed by hand

| Supplementary Layer 1 | % (w/w) | Weight (g) |
|---|---|---|
| Poly(vinylalcohol) (Gohsenol EG-05) solution in Demin water (25.5% wt/wt) | 87.76 | 8.78 |
| Sorbitol | 1.73 | 0.17 |
| Sucrose | 10.51 | 1.05 |
| | 100.00 | 10.00 |

Supplementary Layer 2

Noveon AA-1 powder (modified poly(acrylic acid), Noveon)

| Supplementary Layer 3 | % (w/w) | Weight (g) |
|---|---|---|
| Sorbitol | 11.84 | 4.50 |
| Xylitol | 11.84 | 4.50 |
| Poly(vinylpyrrolidone) (Polyplasdone K90) solution in Demin water 13.8% wt/wt (ISP Corp) | 76.32 | 29.0 |
| | 100.00 | 38.0 |

| Supplementary Layer 4 | % (w/w) | Weight (g) |
|---|---|---|
| Pectin (Kelco) | 25.0 | 2.00 |
| Gantrez MS-955 | 25.0 | 2.00 |
| Sodium Alginate (Keltone LVCR) | 25.0 | 2.00 |
| Modified starch (Cargill 03302) | 25.0 | 2.00 |
| | 100.00 | 8.00 |

PREPARATION OF THE BIOERODIBLE PATCHES

Bioerodible Patch Example 1

A portion of the bioadhesive 1 was placed in a teflon beaker to form an even thin film which was left to dry under ambient conditions over 2 days to form a dry film (ca 0.3 g) A circular disc (ca 1.5 cm diameter) was cut of the dry film generated from drying Bioadhesive layer 1. This had a nicotine total of 2.69 mg calculated. The disc was placed on a grooved metal block and coated with a small amount of a polyvinyl alcohol solution (20% w/w) as a binder for the next layer. The gelatine solution (non-bioadhesive polymer solution 1) at 50 degree centigrade was drawn over this disc and allowed to cool. When cool the sample was detached from the metal block and placed in a jar to prevent the film drying out. The sample was a bioerodible patch with the bioadhesive layer attached to the non bioadhesive layer.

Bioerodible Patch Example 2

Using the same method as Example 1a dry film was obtained from drying bioadhesive layer 2. A circular disc was cut from the dry film. This had a nicotine total of 1.80 mg calculated. The disc was coated as described in example 1. The gelatine sample used was non-bioadhesive polymer solution 2. The sample was a bioerodible patch with the bioadhesive layer attached to the non bioadhesive layer.

Bioerodible Patch Example 3

Wet on Wet Generation of Bioerodible Patch

An alternate approach to the above using a wet bioadhesive layer and then before drying applying a non bioadhesive layer and allowing the film to air dry. The procedure was as follows:

1. On a suitable metal block with a 25 mm wide, 2 mm deep groove, draw down the drug-loaded bioadhesive layer 3 such that the film is approximately 100 μm thick. Use a suitable doctor blade positioned below the upper level of the groove to achieve this. Position the bioadhesive film so that approximately 30 mm of the groove is not covered by the completed film.

2. Place the required amount of non-bioadhesive solution 3 in the uncovered part of the groove. Using a doctor blade, draw down the non-bioadhesive film over the wet bioadhesive film such that the blade is flush with the top of the metal block.

3. Allow to air dry, remove the bilayer film and cut to the required size.

Bioerodible Patch Example 4

The non-bioadhesive layer 3 is cast on to a polycarbonate sheet using a 1 mm film applicator and allowed to set and air dry. Once dried, Supplementary Layer 1 is applied onto the non-bioadhesive layer. Before the layer is completely dry the supplementary layer 2 is dusted on. The partial solvation of the powder aids the compatibility between the layers.

Separately bioadhesive layer 3 is applied to a polycarbonate base using a 300 μm film applicator and dried. The oil loading in the dry film is 29.9% w/w. Once dried, circles 1 cm diameter where cut using a borer.

The small circles of bioadhesive layer were then applied to the powder layer with a small droplet of water to promote adhesion. A 1.5 cm diameter circle is then cut using a borer centred on the bioadhesive film to form concentric disks.

Bioerodible Patch Example 5

Same procedure as Example 4 except using bioadhesive 4 and non bioadhesive layer 4.

Bioerodible Patch Example 6

Consisting of a non-bioadhesive gelatine layer a hydrated supplementary layer consisting bioadhesive powders and a polyaphron containing bioadhesive layer. Bioadhesive layer 3 is applied to a polycarbonate base using a 300 μm film applicator and dried.

Non-bioadhesive layer 3 is cast using a 700 um film applicator onto a polycarbonate sheet and allowed to set but not dry. Powdered mix of Methocel 40-100 (Dow Chemicals) and Gantrez MS-955 (ISP) in a 80:20 blend is then applied. The powder is left to hydrate from the gelatine layer and dry. A small drop of poly(vinylalcohol) (Gohsenol EG-05) 30% solution is applied to the Methocel/Gantrez layer to act as a bridging layer and the preformed bioadhesive layer then affixed.

Bioerodible Patch Example 7

The bioadhesive layer 5 is applied to a polycarbonate base using a 600 μm film applicator and dried. Once dried, circles 1 cm diameter where cut using a borer.

Separately the non-bioadhesive layer 5 is cast on to a polycarbonate sheet using a 0.8 mm film applicator and allowed to set and air dry. Once dried, Supplementary. Layer 3 is applied onto the non-bioadhesive layer (<50 μm). The small circles of bioadhesive layer were then immediately applied followed immediately by Supplementary layer 4 being dusted on in excess and allowed to air dry.

Once dry excess powder is brushed off. A 1.5 cm diameter circle is then cut using a borer centered on the bioadhesive film to form concentric disks.

Two of the inventors tested the system. A patch containing approximately 1.5 mg of nicotine was placed with the active/bioadhesive layer down onto the sublingual area of the mouth and held in place for ten seconds to allow the bioadhesive to attach. After approximately 4 minutes of monitoring both experienced an increase in their resting heart rate and reported a sensory effect similar to that experienced on smoking a cigarette. Subsequent tests with a placebo system did not result in any significant physiological effects. Both reported that the patch dissolved completely after approximately 7 minutes with only minimal taste of nicotine apparent during the experiment.

Bioerodible Patch Example 8

The non-bioadhesive layer 6 is applied to a polycarbonate base using a 700 μm film applicator and allowed to cool for 20 minutes.

A 700 μm film of bioadhesive layer was then cast on top of the non-bioadhesive layer and allowed to cool. Disks 1.5 cm in diameter were then cut through both layers using cork borer. The bioadhesive layer was then applied to a pre formed poly(vinyl acetate) sheet for ease of storage. The patch could then be peeled off of the backing layer as required for use.

The invention claimed is:

1. A bioerodible patch comprising at least one bioadhesive layer and at least one non-bioadhesive layer,
   wherein the bioadhesive layer is a dry film, comprises a mixture of at least one polyaphron dispersion and at least one bioadhesive polymer, and is prepared such that when the patch is placed on the mucosa at least 50% by weight of the bioadhesive layer disintegrates within 20 minutes,
   wherein the non-bioadhesive layer comprises about 5% to about 99% of the patch by weight,
   wherein the polyaphron dispersion comprises at least one pharmaceutically active agent, a continuous phase and a discontinuous phase, wherein the discontinuous phase comprises a pharmaceutically acceptable oil phase,
   wherein the bioadhesive layer comprises from 10 to 50% by weight of pharmaceutically acceptable oil, from 10 to 70% by weight of bioadhesive polymer, and 5 to 30% by weight of plasticizer,
   wherein at least one of the at least one pharmaceutically active agent is poorly water-soluble, wherein the poorly water-soluble pharmaceutically active agent will only dissolve in water in an amount of less than 1% by weight,
   wherein the amount of polyaphron dispersion in the bioadhesive layer is at most 60% by weight of the total bioadhesive layer, the volume fraction of the dispersed phase of the polyaphron dispersion is from 0.7 to 0.97, and
   wherein the polyaphron dispersion is adapted to release individual droplets of the discontinuous phase when the patch disintegrates within a buccal cavity.

2. The patch according to claim 1 wherein the bioadhesive and/or the nonbioadhesive layer comprises a film forming polymer.

3. The patch according to claim 2 wherein the film-forming polymer is selected from polyacrylic acid, pullulan, polyvinylpyrrolidone, polyvinyl alcohol and mixtures thereof.

4. The patch according to claim 1 wherein the bioadhesive polymer is selected from a polyacrylic acid, sodium carboxymethyl cellulose, modified starch, carboxymethyl cellulose, pectin, pullulan, tragacanth, sodium hyaluronate, polyvinylalcohol and mixtures thereof.

5. The patch according to claim 1 wherein the non-bioadhesive layer comprises gelatin and/or carrageenan gum.

6. The patch according to claim 1 wherein the bioadhesive and/or the non-bioadhesive layer comprises a polymer which is capable of undergoing a sol-gel transition as a result of temperature change or crosslinking of the polymer.

7. The patch according to claim 1 wherein the non-bioadhesive layer comprises at least one polyaphron dispersion.

8. The patch according to claim 1 wherein the non-bioadhesive layer comprises a flavouring agent and/or a colouring agent and/or a taste masking agent and/or a disintegrant and/or a plasticizing agent and/or an occlusive agent.

9. The patch according to claim 1 wherein the bioadhesive layer comprises a flavouring agent and/or a colouring agent and/or a taste masking agent and/or a disintegrant and/or an occlusive agent and/or permeation enhancer and/or a saliva stimulant.

10. The patch according to claim 9, wherein the patch comprises a saliva stimulant and wherein the saliva stimulant is citric acid.

11. The patch according to claim 1 wherein the pharmaceutically active agent is selected from an analgesic or anti-inflammatory agent, an anthelmintic, an anti-arrhythmic agent, an anti-coagulant, an anti-depressant, an anti-diabetic agent, an anti-epileptic agent, an anti-fungal agent, an anti-gout agent, an anti-hypertension agent, an anti-malarial, an anti-migraine agent, an anti-muscarinic agent, an anti-neoplastic agent, an anti-protozoal agent, an anti-thyroid agent, an anxiolytic, a sedative, a hypnotic agent or a neuroleptic agent, a corticosteroid, a diuretic, an anti-Parkinsonian agent, a gastro-intestinal agent, a histamine H1-receptor antagonist, a lipid regulating agent, an anti-anginal agent, a thyroid agent, a nutritional agent, an antipyretic agent, an antibacterial agent, an immunosuppressant, an antiviral agent, hypothalmic or a pituitary hormone, a sex hormone, a prostaglandin, a vaccine, a cough suppressant, a local anaesthetic, an immuno-globulin, an antisera, an opioid analgesic, a stimulant, a viral vector for gene therapy, or a therapeutic mixture thereof.

12. The patch according claim 11, wherein the patch comprises a stimulant and wherein the stimulant is nicotine.

13. The patch according claim 11, wherein the patch comprises a an anti-diabetic agent and wherein the anti-diabetic agent is insulin.

14. The patch according to claim 1 comprising from 0.0001% to 60% by weight of a pharmaceutically active agent based on the total weight of the patch.

15. A method for using the patch as defined in claim 1 comprising applying the patch to a mucous membrane of a human or animal in need thereof for the treatment of body tissues, wounds, or conditions selected from the group consisting of depression, diabetes, drug addiction, epilepsy, fungal infection, gout, hypertension, malaria, migraines, Parkinson's disease, cancer, viral infections, bacterial infections, eczema, local or systemic pain, elevated cholesterol, inflammation, insomnia, protozoal infections, tapeworm infection, arrhythmia, thrombosis, angina, allergic reaction, thyroid imbalance, psoriasis, water retention or gastrointestinal infection.

16. A method of making the patch as defined in claim 1 comprising forming a polyaphron dispersion comprising a pharmaceutically active agent; mixing said polyaphron dispersion and a bioadhesive polymer to form the bioadhesive layer and providing on said bioadhesive layer a non-bioadhesive layer.

17. The method of claim 16 wherein the bioadhesive layer is formed by printing, film dipping, film coating, film casting, spin coating, or spraying the bioadhesive polymer onto either a temporary surface or onto a preexisting layer.

18. The method of claim 16 wherein the non-bioadhesive layer is formed by printing, film dipping, film coating, film casting, spin coating, or spraying a non-bioadhesive polymer onto either a temporary surface or onto a pre-existing layer.

19. The bioerodible patch of claim 1, wherein the bioadhesive layer comprises about 1% to about 95% of the patch by weight.

20. The bioerodible patch of claim 1, wherein the polyaphron dispersion comprises less than 3% of a surfactant.

21. The bioerodible patch of claim 1, wherein the non-bioadhesive layer comprises about 0% to about 99% of a film-forming polymer.

22. The bioerodible patch of claim 1, wherein the patch is provided in a unit dosage form.

23. The bioerodible patch of claim 1, wherein the patch comprises 0.05 mg to 500 mg of the at least one pharmaceutically active agent.

24. The bioerodible patch of claim 1, wherein the non-bioadhesive layer is adapted to not significantly adhere to mucosal surfaces or skin.

25. The bioerodible patch of claim 1, wherein the non-bioadhesive layer is positioned to direct the release of the at least one pharmaceutically active agent through the mucosa when the patch is positioned on a mucosal surface.

26. A bioerodible patch comprising at least one bioadhesive layer adjacent to at least one non-bioadhesive layer,
wherein the bioadhesive layer is a dry film, comprises a mixture of at least one polyaphron dispersion having an oil phase and a hydrophilic phase, and at least one bioadhesive polymer, and is prepared such that when the patch is placed on the mucosa at least 50% by weight of the bioadhesive layer disintegrates within 20 minutes,
wherein the amount of polyaphron dispersion in the bioadhesive layer is at most 60% by weight of the total bioadhesive layer, the volume fraction of the dispersed phase of the polyaphron dispersion is from 0.7 to 0.97,
wherein the polyaphron dispersion comprises at least one poorly water-soluble pharmaceutically active agent dissolved in the oil-phase of the polyaphron dispersion wherein the poorly water-soluble pharmaceutically active agent will only dissolve in water in an amount of less than 1% by weight,
wherein the non-bioadhesive layer comprises about 5% to about 99% of the patch by weight,
wherein the bioadhesive layer comprises from 10 to 50% by weight of pharmaceutically acceptable oil, from 10 to 70% by weight of bioadhesive polymer, and 5 to 30% by weight of plasticizer, and
wherein the polyaphron dispersion is adapted to release individual droplets of the discontinuous phase when the patch disintegrates within a buccal cavity.

* * * * *